United States Patent [19]

Haviv et al.

[11] 4,171,434
[45] Oct. 16, 1979

[54] 7-[(PYRIDYLTHIOMETHYL)PHENYL]ACETAMIDOCEPHALOSPORIN DERIVATIVES

[75] Inventors: Fortuna Haviv, Wheeling, Ill.; Abraham Patchornik, Ness Ziona, Israel

[73] Assignee: Yeda Research and Development Co. Ltd., Rehovot, Israel

[21] Appl. No.: 924,940

[22] Filed: Jul. 17, 1978

Related U.S. Application Data

[62] Division of Ser. No. 849,019, Nov. 7, 1977, Pat. No. 4,124,762.

[51] Int. Cl.[2] .............................................. C07D 501/20
[52] U.S. Cl. ........................................ 544/27; 544/21; 424/246
[58] Field of Search ..................................... 544/27, 21

[56] References Cited

U.S. PATENT DOCUMENTS 4,093,804  6/1978  Haviv et al. ............................ 544/27

Primary Examiner—Nicholas S. Rizzo
Attorney, Agent, or Firm—L. Ruth Hattan; Eugene O. Retter; George W. Rauchfuss, Jr.

[57] ABSTRACT

Novel pyridylthiomethyl substituted cephalosporin compounds having the formula

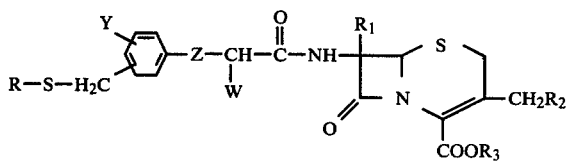

wherein R is 2-pyridyl, 3-pyridyl or 4-pyridyl.

5 Claims, No Drawings

7-[(PYRIDYLTHIOMETHYL)PHENYL] ACETAMIDOCEPHALOSPORIN DERIVATIVES

This is a division, of application Ser. No. 849,019, filed Nov. 7, 1977, now U.S. Pat. No. 4,124,762.

FIELD OF INVENTION

This invention relates to novel cephalosporin derivatives useful as antibiotics and processes for their preparation.

SUMMARY OF INVENTION

Compounds of the following general Formula I are useful as antibiotic agents:

FORMULA I

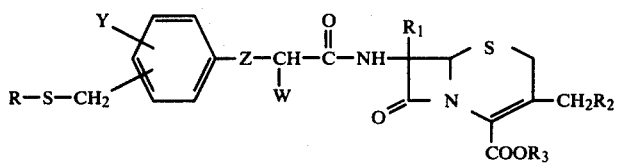

wherein R is 2-pyridyl, 3-pyridyl or 4-pyridyl; Y is selected from hydrogen, chlorine, bromine, a straight or branched lower alkyl group of from 1 to 4 carbon atoms, or an alkoxy group of from 1 to 4 carbon atoms; Z is selected from a bond, oxygen or sulfur. W is selected from hydrogen, methyl, amino, hydroxy, $SO_3H$, or $COOR_4$ wherein $R_4$ is selected from hydrogen or 5-indanyl with the proviso that when Z is oxygen or sulfur, W is other than hydroxy; $R_1$ is hydrogen or methoxy; $R_2$ is hydrogen, acetoxy; 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,3,4-triazol-2-ylthio; 5-methyl-1,3,4-triazol-2-ylthio; 1,2,3-triazol-5-ylthio; $R_3$ is hydrogen, a cation of an alkali metal or an alkaline earth metal, ammonium or organic ammonium cations, a straight or branched lower alkyl group of from 1 to 4 carbon atoms, a straight or branched alkanoyloxymethyl group in which the alkanoyl moiety has from 2 to 5 carbon atoms, and is straight or branched, an alkanoylaminomethyl group in which the alkanoyl moiety is straight or branched and has from 2 to 5 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, a p-(alkanoyloxy)benzyl group in which the alkanoyl moiety is straight or branched and has from 1 to 4 carbon atoms; an aminoalkanoyloxy methyl group in which the alkanoyl moiety has from 2 to 15 carbon atoms and the amino nitrogen may be mono- or di-substituted with a straight or branched lower alkyl group having from 1 to 4 carbon atoms; and pharmaceutically acceptable salts and individual optical isomers thereof.

The non-toxic acid addition salts of the compounds such as mineral acid addition salts, for example, hydrogen chloride, hydrogen bromide, hydrogen iodide, sulfate, sulfamate and phosphate and organic acid addition salts, for example maleate, acetate, citrate, oxalate, succinate, benzoate, tartrate, fumarate, malate, mandelate and ascorbate, are also included within the scope of this invention.

DETAILED DESCRIPTION OF INVENTION

In general Formula I the substituent group as represented by $R_3$ in addition to being hydrogen, a cation or a lower alkyl group may also be alkanoyloxymethyl as represented by the structure:

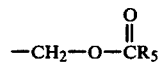

wherein $R_5$ is selected from a straight or branched lower alkyl group of from 1 to 4 carbon atoms; alkanoylaminomethyl or alkoxycarbonylaminomethyl as represented by the structure:

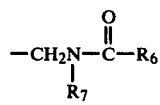

wherein $R_6$ represents a straight or branched lower alkyl group of from 1 to 4 carbon atoms or a straight or branched alkoxy group of from 1 to 4 carbon atoms, and $R_7$ is selected from hydrogen and a lower alkyl group of from 1 to 4 carbon atoms; p-(alkanoyloxy)benzyl as represented by the structure:

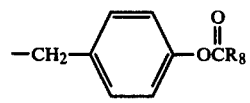

wherein $R_8$ is a straight or branched lower alkyl of from 1 to 4 carbon atoms; and aminoalkanoyloxymethyl as represented by the group:

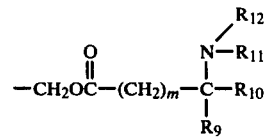

wherein m is 0 to 5, each of $R_9$ and $R_{10}$ is selected from hydrogen or lower alkyl of from 1 to 4 carbon atoms, and each of $R_{11}$ and $R_{12}$ is selected from hydrogen or a straight or branched lower alkyl group of from 1 to 4 carbon atoms.

Illustrative examples of straight or branched lower alkyl groups of from 1 to 4 carbon atoms which Y, $R_5$, $R_6$, $R_8$, $R_{11}$ and $R_{12}$ may represent are methyl, ethyl, n-propyl, isopropyl, n-butyl and tert-butyl.

Examples of lower alkyl groups of from 1 to 4 carbon atoms which $R_7$, $R_9$ and $R_{10}$ may represent are methyl, ethyl, n-propyl and n-butyl.

Examples of lower alkoxy groups which Y may represent are methoxy, ethoxy, n-propoxy and n-butoxy.

In the compounds of general Formula I the substituent group $R_2$ represents, in addition to hydrogen and acetoxy heterocyclicthio groups selected from 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio and 1,2,3-triazol-5-ylthio as represented by the following respective structures:

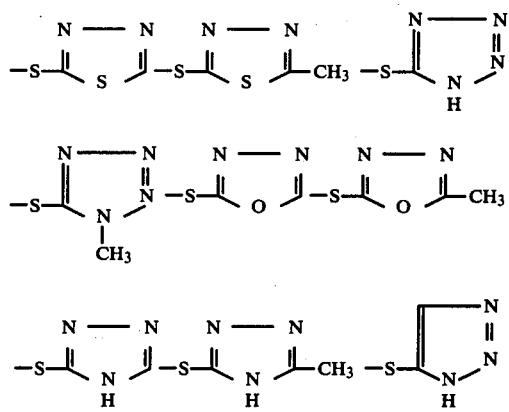

Preferred compounds of this invention are compounds of Formula I wherein W is hydrogen, amino, hydroxy, —COOH or —$SO_3H$. More preferred compounds of this invention are compounds of Formula I wherein W is hydrogen or amino. Even more preferred compounds are those of Formula I wherein Z is a bond and Y is hydrogen. Compounds wherein R is 4-pyridinyl or 2-pyridinyl are also preferred.

The compounds of Formula I are prepared by treatment of a derivative of Formula II with a derivative of Formula III

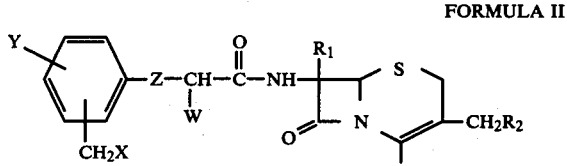

FORMULA II

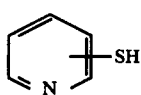

wherein Y, Z, W, $R_1$, $R_2$ and $R_3$ have the same meaning as described in Formula I and X is a halogen atom such as chlorine, bromine or iodine.

The reaction between a compound of Formula II and a compound of Formula III to give a compound of Formula I takes place when equimolar amounts of the reagents are combined in a suitable solvent. Suitable solvents include dimethyl formamide, acetone, ethyl acetate, acetonitrile, methanol, ethanol. The temperature of the reaction may vary from 0° to 100° C. and the reaction time may vary from about 0.5 hour to 10 hours. The product of the reaction of Formula I may be obtained upon removal of the solvent or by precipitation upon combination of the reaction solution with a solvent in which the product is insoluble.

The compounds of Formula II may be used in situ without the need of prior isolation when prepared by the treatment of a compound of Formula III with the product obtained upon coupling a compound of Formula IV with an acid of Formula V or a functional equivalent thereof

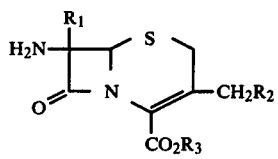
Formula IV

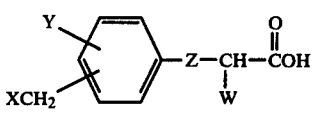
Formula V wherein $R_1$, $R_2$, $R_3$, X, Y, Z and W are as described above.

Compounds of Formulas II and V have been described in U.S. Pat. Nos. 3,919,206; 3,948,904; 4,026,887. Compounds of Formula III are commercially available or may be readily prepared by known procedures.

The compounds of general Formula IV, that is, 7-aminocephalosporanic acid and 7-aminodesacetoxycephalosporanic acid and derivatives thereof are commercially available or may be obtained from Penicillin G, cephalosporin C or cephamycin C by processes known in the art. For example, compounds of Formula IV wherein $R_7$ is methoxy may be prepared as described by M. Sletzinger et al., J. Am. Chem. Soc., 94, 1408 (1972).

Compounds of Formula IV may also be prepared as described in U.S. Pat. Nos. 3,948,904 and 4,026,887.

When the subtituent group W in the above Formula V represents an amino group suitable blocking groups, for example, tert-butoxycarbonyl, or carbobenzyloxy are employed to protect the amino function. Such blocking groups are removed after the coupling reaction by methods generally known in the art, for example, as described by Lemieux et al., in U.S. Pat. No. 3,657,232.

The preparation of a compound of Formula V wherein W is —COOindanyl may be carried out by reacting the corresponding compound of Formula V wherein W is —COOH with one mole of 5-indanol in an inert solvent such as chloroform, dichloromethane, dimethylformamide, in the presence of N,N'-dicyclohexylcarbodiimide at a pH of about 2.5 and a temperature of from 20° to 30° C. The product is isolated upon filtration of the N,N'-dicyclohexyl urea formed and subsequent removal of the solvent.

Functional equivalents of the acids as represented by Formula V include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester of thioester, for example, with p-nitrophenol, 2,4-dinitrophenol, or thioacetic acid, may be used, or the free acid as represented by Formula V may be coupled with the 7-aminocephalosporanic acid derivative as represented by Formula IV after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The coupling reaction between compounds of Formula IV and Formula V is generally carried out in the presence of a solvent, such as, ethyl acetate, acetone, dioxane, acetonitrile, chloroform, ethylene chloride, tetrahydrofuran and dimethylformamide and optionally in the presence of a base such as sodium bicarbonate, triethylamine N,N-dimethylaniline. The temperature of the reaction may vary from $-10°$ to $100°$ C., and the reaction time may vary from about ½ hour to 10 hours. The cephalosporin products are isolated by conventional methods.

The salt forms of Formula I wherein $R_3$ is a pharmaceutically acceptable cation are prepared in the manner recognized in the art and may be formed in situ or by reacting the corresponding acid with base, for example, sodium bicarbonate or triethylamine.

The compounds of Formula I wherein $R_2$ is selected from a heteroarylthiol residue may also be prepared by the reaction of a compound of Formula I wherein $R_2$ is acetoxy namely Formula VI with an appropriate heteroarylthiol of Formula VII as schematically described below OH, COOH or $SO_3H$ are also included within the scope of this invention.

The novel compounds of this invention are useful as antibiotic agents as demonstrated by their activity against gram positive and gram negative bacteria in vitro and in vivo and fungi. The compounds of this invention are particularly useful in that they possess a longer duration of activity than many of the well known cephalosporin compounds. Illustrative examples of bacteria against which the compounds of this invention are active are *Staphylococcus aureus, Salmonella schottmulleri, Klebsiella pneumoniae, Diplococcus pneumonia,* and *Streptococcus pyogenes.*

The compounds of this invention may be administered alone or in the form of pharmaceutical preparations either orally, parenterally or topically. They may be administered to warm blooded animals, that is, birds and mammals, for example, felines, canines, bovines, equines, and humans. For oral administration the compounds may be administered in the form of tablets, capsules or pills or in the form of elixirs or suspensions. For parenteral administration they are best used in the form of a sterile aqueous solution which may contain other solutes, for example, enough saline or glucose to make the solution isotonic. For topical administration the compounds may be incorporated into creams or

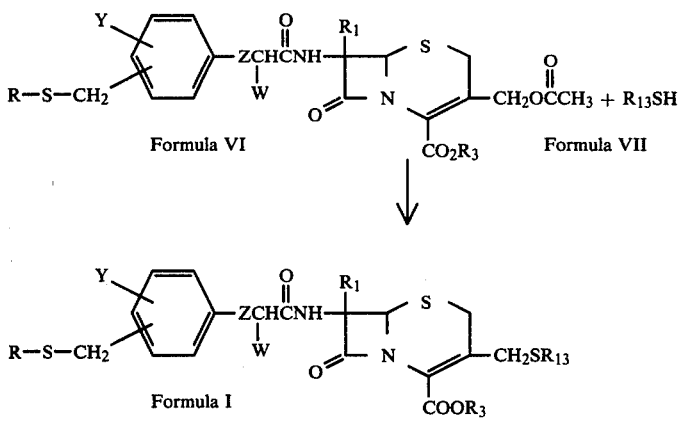

wherein Y, W, Z, R, $R_1$ and $R_3$ are described above and $R_{13}$-S- is a heteroarylthio residue selected from 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,3,4-triazol-2-ylthio; 5-methyl-1,3,4-triazol-2-ylthio; and 1,2,3-triazol-5-ylthio.

The reaction is generally carried out in the presence of a solvent. Suitable solvents include water, methanol, ethanol, dimethylformamide, and dimethylsulfoxide. The reaction is carried out by mixing in the hereinabove mentioned solvent a compound of Formula VI with a compound of Formula VII, in such a way that the compound of Formula VII may be present in a non-stoichiometric excess relative to the compound of Formula VI. The reaction temperature may vary from about 25° C. to 100° C. and the reaction time may vary from about ½ hour to 10 hours. The reaction may be carried out in the presence of a base such as sodium carbonate, sodium bicarbonate, or triethylamine. The product of the reaction is isolated by conventional methods known in the art.

The individual optical isomers of the compounds of general Formula I wherein W represents methyl, $NH_2$, ointments.

GENERAL PROCEDURES FOR THE PREPARATION OF COMPOUNDS OF FORMULA I

PROCEDURE I

To a solution of a compound of Formula II in 5–10 ml of dimethylformamide an equimolar amount of a compound of Formula III is added.

The solution is stirred at about 25° C. for 30 minutes and at 55° C. for three hours, and is then added to 200 ml of dichloromethane. The mixture is stirred for 30 minutes. The precipitated solid is filtered, washed with dichloromethane, and dried to give the product isolated as the hydrohalide salt.

PROCEDURE II

To a cold solution of sodium bicarbonate (2 equivalents) and a compound of Formula IV (1 equivalent) in a mixture of three parts of water to two parts of acetone, is added a compound of Formula V in one part of acetone.

The solution is stirred for 30 minutes at about 25° C. and is then flash concentrated until all the acetone has been removed. To the obtained solution a compound of Formula III (1 equivalent) is added. The solution is stirred at room temperature for two hours. During this time a solid precipitate is formed which is filtered, washed with water and dried to give the desired compound of Formula I.

EXAMPLE 1

3-[(Acetyloxy)methyl]-8-oxo-7-[[[4-[(4-pyridinylthio)-methyl]phenyl]acetyl]amino]-5-thia-1-azabicyclo[4.2.-0]oct-2-ene-2-carboxylic acid hydrochloride NMR (DMSO-$D_6$+$D_2O$) ppm [δ] 2.10 (s,3), 3.6 (broad s, 2), 4.6 (s, 2), 4.88 (q, 2), 5.13 (d, 1), 5.75 (d, 1), 7.1–8.8 (m, 8).

When in the procedure of Example 1 an appropriate amount of a chloromethyl substituted cephalosporin derivative of Formula II listed in the following Table I is substituted for 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid the respective [(pyridinylthio)methyl]phenyl]acetyl]-substituted cephalosporin product listed in Table I is obtained.

TABLE 1

| CHLOROMETHYL SUBSTITUTED CEPHALOSPORIN DERIVATIVE | MERCAPTO PYRIDINE | PYRIDYLTHIO SUBSTITUTED CEPHALOSPORIN PRODUCT |
|---|---|---|
| 3-[(1-methyltetrazol-5-ylthio)-methyl]-7-[[2-[4-(chloromethyl)-phenyl]acetyl]amino]-8-oxo-5-thia-1-azabicyclo[4.2.0]oct-2-ene-2-carboxylic acid | 4-mercaptopyridine | 3-[[(1-methyl-1H-tetrazol-5-yl)thio]-methyl]-8-oxo-7-[[[4-[(4-pyridinyl-thio)methyl]phenyl]acetyl]amino]-5-thia-1-azabicyclo[4.2.0]oct-2-ene-2-carboxylic acid |
| 3-[(acetyloxy)methyl]-7-[[2-[4-(chloromethyl)phenyl]-2-hydroxyacetyl]amino]-8-oxo-5-thia-1-azabicyclo[4.2.0]oct-2-ene-2-carboxylic acid | 4-mercaptopyridine | 3-[(acetyloxy)methyl]-7-[(hydroxy[4-[(4-pyridinylthio)methyl]phenyl]-acetyl]amino]-8-oxo-5-thia-1-azabicyclo[4.2.0]oct-2-ene-2-carboxylic acid |
| 3-[(acetyl)methyl]-7-[[2-[4-(chloromethyl)phenyl]-2-carboxyacetyl]amino]-8-oxo-5-thia-1-azabicyclo[4.2.0]oct-2-ene-2-carboxylic acid | 3-mercaptopyridine | 3-[(acetyloxy)methyl]-7-[[carboxy-(3-[(4-pyridinylthio)methyl]phenyl]-acetyl]amino]-8-oxo-5-thia-1-azabicyclo[4.2.0]oct-2-ene-2-carboxylic acid |
| 3-[(acetyloxy)methyl]-7-[[2-[4-(chloromethyl)phenyl]-2-sulfoacetyl]amino]-8-oxo-5-thia-1-azabicyclo[4.2.0]oct-2-ene-2-carboxylic acid | 3-mercaptopyridine | 3-[(acetyloxy)methyl]-8-oxo-7-[[(4-[(3-pyridinylthio)methyl]phenyl]-sulfoacetyl]amino]-5-thia-1-azabicyclo[4.2.0]oct-2-ene-2-carboxylic acid |
| 3-[(2-methyl-1,3,4-thiadiazol-5-ylthio)methyl]-7-[[2-[4-(chloromethyl)phenyl]-2-aminoacetyl]amino]-8-oxo-5-thia-1-azabicyclo[4.2.0]oct-2-ene-2-carboxylic acid | 2-mercaptopyridine | 7-[[amino[4-[(2-pyridinylthio)methyl]-phenyl]acetyl]amino]-3-[[(5-methyl-1,3,4-thiadiazol-2-yl)thio]methyl]-8-oxo-5-thia-1-azabicyclo[4.2.0]-oct-2-ene-2-carboxylic acid |
| 3-[(acetyloxy)methyl]-7-[[2-[4-(chloromethyl)phenyl]-2-aminoacetyl]amino]-8-oxo-5-thia-1-azabicyclo[4.2.0]oct-2-ene-2-carboxylic acid 2,2-dimethyl-1-oxopropoxymethyl ester | 2-mercaptopyridine | 3-[(acetyloxy)methyl]-7-[[amino-[4-[(2-pyridinylthio)methyl]phenyl]-acetyl]amino]-8-oxo-5-thia-1-azabicyclo[4.2.0]oct-2-ene-2-carboxylic acid |
| 3-[(acetyloxy)methyl]-7-[[2-[2-(chloro)-4-(chloromethyl)phenyl]-acetyl]amino]-8-oxo-5-thia-1-azabicyclo[4.2.0]oct-2-ene-2-carboxylic acid | 4-mercaptopyridine acetyl]amino]-8-oxo-5-thia-1-azabi- | 3-[(acetoxy)methyl]-7-[[[2-chloro-4-[(4-pyridinylthio)]methyl]phenyl]-cyclo[4.2.0]oct-2-ene-2-carboxylic acid |
| 3-[(acetyloxy)methyl]-7-[[2-[4-(chloromethyl)phenoxy]acetyl]-amino]-8-oxo-5-thia-1-azabicyclo[4.2.0]oct-2-ene-2-carboxylic acid | 3-mercaptopyridine | 3-[(acetyloxy)methyl]-8-oxo-7-[[[4-(3-pyridinylthio)phenoxy]acetyl]-amino]-5-thia-1-azabicyclo[4.2.0]-oct-2-ene-2-carboxylic acid |
| 3-[(2-methyl-1,3,4-thiadiazol-5-ylthio)methyl]-7-[[2-[4-(chloromethyl)phenyl]-2-hydroxyacetyl]-amino]-8-oxo-5-thia-1-azabicyclo-[4.2.0]oct-2-ene-2-carboxylic acid | 2-mercaptopyridine | 7-[[hydroxy[2-[(4-pyridinylthio)-methyl]phenyl]acetyl]amino]-3-[[(5-methyl-1,3,4-thiadiazol-2-yl)thio]-methyl]-8-oxo-5-thia-1-azabicyclo-[4.2.0]oct-2-ene-2-carboxylic acid |
| 3-[(acetyloxy)methyl]-7-[[2-[4-(chloromethyl)phenyl]thio]acetyl]-amino]-8-oxo-5-thia-1-azabicyclo-[4.2.0]oct-2-ene-2-carboxylic acid | 2-mercaptopyridine | 3-[(acetyloxy)methyl]-8-oxo-7-[[[4-[(2-pyridinylthio)methyl]phenyl]-acetyl]amino]-5-thia-1-azabicyclo-[4.2.0]oct-2-ene-2-carboxylic acid |

The title compound is obtained in 47.5% yield when prepared according to Procedure I when the reagents used are 3-[(acetyloxy)methyl]-7-[[2-[4-(chloromethyl)-phenyl]acetyl]amino]-8-oxo-5-thia-1-azabicyclo[4.2.-0]oct-2-ene-2-carboxylic acid (a compound of Formula II) and 4-mercaptopyridine (a compound of Formula III).

EXAMPLE 2

3-[(Acetyloxy)methyl]-8-oxo-7-[[[4-(2-pyridinylthio)-methylphenyl]acetyl]amino]-5-thia-1-azabicyclo[4.2.-0]oct-2-ene-2-carboxylic acid hydrochloride The title compound is prepared in 69% yield by the same procedure as that described in Example 1, when 2-mercaptopyridine is used instead of 4-mercaptopyridine.

NMR (DMSO-D$_6$+D$_2$O) ppm (δ) 2.10 (s,3), 3.6 (broad s,2), 4.58 (s,2), 4.91 (q,2), 5.13 (d,1), 5.77 (d,1), 7.1-8.9 (m,8).

We claim:

1. A compound of the formula

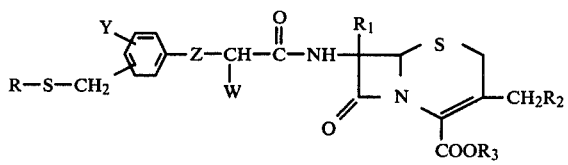

wherein R is 2-pyridyl, 3-pyridyl or 4-pyridyl; Y is hydrogen, chlorine, bromine, a straight or branched lower alkyl group of from 1 to 4 carbon atoms, or an alkoxy group of from 1 to 4 carbon atoms; Z is a bond, oxygen or sulfur; W is hydrogen, methyl, amino, hydroxy, XO$_3$H, or COOR$_4$ wherein R$_4$ is hydrogen or 5-indanyl with the proviso that when Z is oxygen or sulfur, W is other than hydroxy; R$_1$ is hydrogen or methoxy; R$_2$ is 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio or 1,2,3 triazol-5-ylthio; R$_3$ is hydrogen, a cation of an alkali metal or an alkaline earth metal, ammonium, a straight or branched lower alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, a p-(alkanoyloxy(benzyl group in which the alkanoyl moiety is straight or branched and has from 2 to 5 carbon atoms; an aminoalkanoyloxy methyl group in which the alkanoyl moiety has from 2 to 15 carbon atoms and the amino nitrogen may be mono- or di-substituted with a straight or branched lower alkyl group having from 1 to 4 carbon atoms; and pharmaceutically acceptable salts and individual optical isomers thereof.

2. A compound of claim 1 wherein W is hydrogen, amino, hydroxy, CO$_2$H, SO$_3$H.

3. A compound of claim 2 wherein Z is a bond.

4. A compound of claim 3 wherein Y is hydrogen.

5. A compound of claim 1 which is 3-[[(1-methyl-1H-tetrazol-5-yl)thio]methyl]-8-oxo-7-[[[4-[(4-pyridinylthio)methyl]phenyl]acetyl]amino]-5-thia-1-azabicyclo[4.2.0]oct-2-ene-2-carboxylic acid or a pharmaceutically acceptable salt thereof.

* * * * *